United States Patent [19]

McAfee et al.

[11] Patent Number: 5,117,830
[45] Date of Patent: Jun. 2, 1992

[54] METHOD OF DETERMINING VIABILITY OF TISSUE

[75] Inventors: Donald A. McAfee, Richmond, Va.; Luiz Belardinelli, Gainesville, Fla.

[73] Assignee: Whitby Research, Inc., Richmond, Va.

[21] Appl. No.: 610,544

[22] Filed: Nov. 8, 1990

[51] Int. Cl.⁵ .................................... A61B 6/00
[52] U.S. Cl. .................................... 128/654
[58] Field of Search ............ 424/1.1, 9; 128/653 AF, 128/653 CA; 600/304

[56] References Cited

U.S. PATENT DOCUMENTS

| | | | |
|---|---|---|---|
| 4,788,500 | 11/1988 | Patz et al. | 128/653 AF |
| 4,803,977 | 2/1989 | Kremer, Jr. | 600/3 |
| 4,824,660 | 4/1989 | Angello et al. | 424/9 |
| 4,855,300 | 8/1989 | Nandi et al. | 514/264 |
| 4,904,472 | 2/1990 | Belardinelli et al. | 514/263 |

Primary Examiner—C. Fred Rosenbaum
Assistant Examiner—Sharon Finkel
Attorney, Agent, or Firm—Walter A. Hackler; Richard J. Hammond

[57] ABSTRACT

A method and composition for determining the viability of tissue in a region of an organism having a vascular circulatory system that supplies blood to said region including the steps of dilating said vascular circulation system by introducing adenosine or an adenosine agonist into said vascular circulation system in order to increase the flow of blood into said region; introducing a blood flow marking medium into said region; alleviating the non-dilating effects of adenosine or said adenosine agonist by introducing an $A_1$ adenosine receptor antagonist into said vascular circulatory system; and determining the amount of marking medium in said region. A composition is disclosed which includes the combination of adenosine or an adenosine agonist in combination with an $A_1$ adenosine receptor which may be:

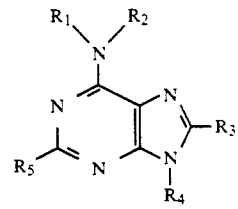

wherein $R_1$ is hydrogen or $R_2$; $R_2$ is selected from the group consisting of endo-2-norbornyl or cyclopentyl; $R_3$ is selected from the group consisting of hydrogen, halogen, amine, carboxy, alkyl radicals having 1 to 10 carbon atoms, cycloalkyl radicals having from 3 to 8, preferably 5 to 6, ring carbon atoms, thio, sulfonate, sulfonamide, sulfon, sulfoxamide, phenyl, alkyl-substituted amine, and cycloalkyl substituted amine, $R_4$ is selected from the group consisting of benzyl, phenyl, and alkyl groups comprising from 1 to 4 carbon atoms, wherein said alkyl group can be substituted with oxygen, for instance ethers and alcohols; and $R_5$ is selected from the group consisting of hydrogen; hydroxy; sulfonate; halogen; alkoxy and cycloalkoxy groups comprising 1 to 6 carbon atoms.

21 Claims, No Drawings

METHOD OF DETERMINING VIABILITY OF TISSUE

The present invention is generally directed to a method for determining the viability of tissue in an organism having a vascular circulatory system and a composition for use in such a method. More particularly, the method and composition of the present invention is directed to the pharmacological vasodilation of vascular systems with the introduction of adenosine or an adenosine agonist in combination with an $A_1$ adenosine receptor antagonist and thallium-201 scintigraphy.

Thallium-201 myocardial profusion imaging is a valuable tool in the assessment of patients who cannot adequately exercise. Heretofore, thallium-201 scintigraphy has been used in combination with dipyridamole and adenosine. Dipyridamole produces an increase in coronary blood flow by blocking the metabolism and uptake of adenosine which leads to a subsequent increase in both myocardial and arterial wall adenosine concentrations. It is believed that dipyridamole only has an indirect vasal dilatory effect. On the other hand, endogenous adenosine is believed to be a direct mediator of coronary dilation.

Heretofore vasodilation produced by adenosine has been used to induce controlled hypotension in patients undergoing surgery and is relatively safe in view of its short half-life which is believed to be less than two seconds. Thus, its effect will disappear much faster on cessation of drug infusion as compared to dipyridamole which has a significantly longer half-life.

While the use of dipyridamole is common as a pharmacologic stress agent for patients undergoing thallium-201 scintigraphy, it is limited by rare but potentially serious side effects which include myocardial ischemia, cardiac arrhythmia, and sudden death.

Adenosine, a nucleoside, has been shown to be a potent vasodilator, except in the kidney, and is thought to block calcium uptake by vascular smooth muscle or to increase the cyclic adenosine monophosphate concentration leading to coronary artery vasodilation.

The source of adenosine in the heart is myocardial adenosine triphosphate and cyclic adenosine monophosphate. Adenosine release parallels metabolic activity, increases heart rate, and stimulates ventilation but does not alter airway resistance.

Use of adenosine, however, has been shown to produce a number of cardiovascular, respiratory, central nervous system, and gastrointestinal side effects. These include facial flushing, headache, sweating palpitations, chest pains, hypotension, shortness of breath/dyspnea, chest pressure, hyperventilation, head pressure, lightheadedness, dizziness, tingling in arms, numbness, apprehension, blurred vision, burning sensation, heaviness in arms, neck and back pain, nausea, metallic taste, tightness of throat, and pressure in the groin.

The method and composition of the present invention substantially decrease the hereinabove noted side effects through alleviating the $A_1$ effects of adenosine as an $A_1$ antagonist while maintaining $A_2$ vasodilation activity of adenosine.

SUMMARY OF THE INVENTION

A method, in accordance with the present invention, for determining the viability of tissue in a region of an organism having a vascular circulatory system which supplies blood to the region, includes the steps of dilating the vascular circulation system by introducing adenosine or an adenosine agonist into the vascular circulation system in order to increase the flow of blood into the region, introducing a blood flow marking medium into the region and introducing an $A_1$ adenosine receptor antagonist into the vascular circulatory system. Thereafter, the model marking medium in the region is determined which relates to the viability of tissue in the region.

A composition suitable for use in the method of the present invention includes adenosine or an adenosine agonist in combination with an $A_1$ adenosine receptor antagonist in an amount sufficient to alleviate all effects of adenosine or said adenosine agonist except coronary vasodilation when the composition is administered to a mammal. Generally, compositions in accordance with the present invention include compounds represented by the formula:

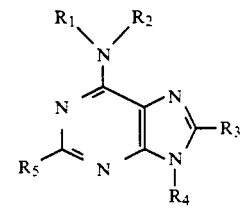

wherein $R_1$ is hydrogen or $R_2$; $R_2$ is selected from the group consisting of endo-2-norbornyl or cyclopentyl; $R_3$ is selected from the group consisting of hydrogen, halogen, amine, carboxy, thio, sulfonate, sulfonamide, sulfone, sulfoxamide, phenyl, alkyl-substituted amine, cycloalkyl-substituted amine, alkyl radicals having from 1 to 10 carbon atoms, and cycloalkyl radicals having from 3 to 8, preferably 5 to 6, ring carbon atoms; $R_4$ is selected from the group consisting of benzyl, phenyl, and alkyl groups comprising from 1 to 4 carbon atoms, wherein said alkyl group can be substituted with oxygen, for example ethers and alcohols; and $R_5$ is selected from the group consisting of hydrogen; hydroxy; sulfonate; halogen; alkoxy and cycloalkoxy groups comprising 1 to 6 carbon atoms, wherein said alkoxy and cycloalkoxy groups can be substituted with phenyl; and amine, wherein said amine can be substituted with alkyl, cycloalkyl, or phenyl.

More specifically compositions in accordance with the present invention encompass the combination of adenosine or adenosine agonist with an $N^6$-norbornyl substituted adenosine derivative in an amount sufficient to reduce the amount of the adenosine or adenosine agonist necessary to dilate a vascular circulatory system when the composition is administered to a mammal.

Advantageously, the $N^6$-norbornyl substituted adenine introduced into the vascular circulation system also reduces the amount of adenosine or adenosine agonist necessary to dilate the vascular circulatory system than if the $N^6$-norbornyl substituted adenine were not introduced into the vascular circulation system.

More particularly, the method of composition of the present invention may include the use of a marking medium selected from the group consisting of thallium-201 and rubidium-82 and more specifically the $N^6$-norbornyl substituted adenine may be 9-methyl-n-6-endo norbornyl adenine.

DETAILED DESCRIPTION

The preferred embodiment of the present invention is directed to a composition comprising adenosine or an adenosine agonist combination with an $A_1$ adenosine receptor antagonist and the use of the $A_1$ in a method for determining the viability of tissue, which also includes the introduction of adenosine.

Adenosine receptors have been divided into two subtypes, based on adenylate cyclase activity: $A_1$ ($R_i$) receptors mediate inhibition and $A_2$ ($P_a$) receptors mediate stimulation of adenylate cyclase activity. Some $N^6$-substituted adenosine analogs, like $N^6$-R-phenyl isopropyl adenosine (R-PIA) have very high affinity for $A_1$ adenosine receptors, but at $A_2$ receptors 5'-N-ethyl-carboxamido-adenosine (NECA) is more potent than $N^6$-substituted analogs Alkylxanthines, such as caffeine and theophylline, are the best known antagonists at adenosine receptors.

The use of adenosine in myocardial imaging or scintigraphy with thallium-201 or rubidium-82 has been investigated. For example, see Verani, Mario S. et. al., "Diagnosis of Coronary Artery Disease by Controlled Coronary Vasodilation with Adenosine and Thallium-201 Scintigraphy in Patients Unable to Exercise," Circulation, Vol. 82, No. 1, July 1990, pp. 80-86; Siffring, Patricia A., et.al., "Myocardial Uptake and Clearance of TI-201 in Healthy Subjects: Comparison of Adenosine-induced Hyperemia and Exercise Stress," Radiology. Vol. 173 No. 3, 1989, pp. 769-774.

The principle of vasodilator thallium-201 myocardial imaging is the dilatation of the vascular circulatory system in order to increase coronary blood flow and thallium-201 uptake to normal areas of myocardium, whereas areas of myocardium served by coronary artery with hemodynamically significant coronary artery narrowing experiences a reduced flow reserve and hence less thallium-201 uptake. Thallium-201 is a preferred blood flow marking medium well-known in the art, although other effective blood flow marking mediums may be used in accordance with the present invention, including rubidium-82.

As hereinbefore mentioned, thallium-201 myocardial imaging is found useful in evaluating patients with peripheral vascular disease who cannot perform adequate exercise due to myocardial ischemia. Thus, the determination of the amount of marking medium upon vasodilation enables the identification of patients with significant coronary artery narrowing and protection of areas by appropriate medical therapy.

In accordance with the present invention, adenosine is infused at a predetermined rate into the region to be investigated and hemodynamic measurements are made to determine aortic pressure.

Following the initial infusion of adenosine, thallium-201 is injected and the adenosine infusion continues. Simultaneous with or subsequent to the initial introduction of adenosine, $N^6$-norbornyl substituted adenine is introduced into the region and myocardial scintigraphic recordings started utilizing conventional apparatus, including a standard gamma camera, suitable collimators and associated equipment for producing digitized images. In accordance with conventional protocol for hemodynamic measurements, scintiscans are repeated periodically for the duration of each experiment.

The compounds of this invention are represented by the formula:

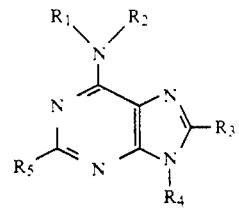

wherein $R^1$ is hydrogen or $R_2$; $R_2$ is selected from the group consisting of endo-2-norbornyl or cyclopentyl; $R_3$ is selected from the group consisting of hydrogen, halogen, amine, carboxy, alkyl radicals having 1 to 10 carbon atoms, cycloalkyl radicals having from 3 to 8, preferably 5 to 6, ring carbon atoms, thio, sulfonate, sulfonamide, sulfon, sulfoxamide, phenyl, alkyl-substituted amine, and cycloalkyl substituted amine; $R_4$ is selected from the group consisting of benzyl, phenyl, and alkyl groups comprising from 1 to 4 carbon atoms, wherein said alkyl group can be substituted with oxygen, for instance ethers and alcohols; and $R_5$ is selected from the group consisting of hydrogen; hydroxy; sulfonate; halogen; alkoxy and cycloalkoxy groups comprising 1 to 6 carbon atoms, wherein said alkoxy and cycloalkoxy groups can be substituted with phenyl; and amine, wherein said amine can be substituted with phenyl and alkyl and cycloalkyl groups comprising 1 to 6 carbon atoms.

The preferred compounds are those wherein $R^1$ is hydrogen; wherein $R_2$ is endo-2-norbornl or cyclopentyl; wherein $R_3$ is bromine, chlorine, amino, hydrogen, thio, cyclopentyl or cyclopentylamine; wherein $R_4$ is methyl, ethyl, 2-hydroxyethyl, phenyl, or 2-hydroxyethoxy methyl; and wherein $R_5$ is hydrogen, hydroxy or chlorine.

The following is a list of compounds useful in the practice of the present invention. This list is intended to be illustrative and the scope of the invention is not limited to compounds named therein:

$N^6$-cyclopentyl-9-methyl adenine (MA)
$N^6$-3-9-MA
$N^6$-(endo-2-norbornyl)-9-MA
$N^6$-1-(2-thienyl)-2-butyl-9-MA
$N^6$-(endo-2-norbornyl)-2-chloro-9-MA
$N^6$-(endo-2-norbornyl)-8-cyclopentyl-9-MA
$N^6$-(endo-2-norbornyl)-8-hydroxy-9-MA
$N^6$-(endo-2-norbornyl)-8-bromo-9-MA
$N^6$-(endo-2-norbornyl)-8-amino-9-MA
$N^6$-(endo-2-norbornyl)-8-carboxy-9-MA
$N^6$-cyclopentyl-8-cyclopentyl-9-MA
$N^6$-(endo-2-norbornyl)-9-[(2-hydroxyethoxy)methyl] adenine
$N^6$-(endo-2-norbornyl)-8-thio-9-MA
$N^6$-(endo-2-norbornyl)-8-chloro-9-MA
$N^6$-(endo-2-norbornyl)-8-sulfonate-9-MA sodium salt
$N^6$-(endo-2-norbornyl)-2-hydroxy-9-MA
$N^6$-(endo-2-norbornyl)-8-cyclopentylamine-9-MA
$N^6$-(endo-2-norbornyl)-8-propylamine-9-MA
$N^6$-(endo-2-norbornyl)-9-phenyl adenine The preparation of 9-methyl adenines is well-known. See R. K. Robins, K. J. Dille, and B. E. Christensen, J. Org. Chem., 19, 930 (1954); R. K. Robins and H. H. Lin, J. Am. Chem. Soc., 79, 490 (1957; and J. A. Montgomery and Carroll Temple, Jr., J. Am. Chem. Soc. 79, 5238 (1957).

Preparation of $N^6$-cyclopentyl-9-methyl adenine

To prepare $N^6$-cyclopentyl-9-methyl adenine the following additional steps were taken. A mixture of 6-chloro-9-methyl adenine (0.82 g), cyclopentyl-amine (0.52 ml), triethylamine (0.53 ml) and ethanol (60 ml), was refluxed for 24 hours. The solution was concentrated in vacuo to a yellow syrup. The syrup was passed through a C-18 column to give 0.78 g or 74% yield of with m.p. 108°–109° C. $^1$HNMR(Me$_2$SO-d6): δ1–2)m,9 H); 3.7(S, Ch$_3$); 7.6(d,NH); 8.1(S,1H; 8.2(S,1H).

Preparation of $N^6$-(endo-2-norbornyl)-8-bromo-9-MA

To a stirred suspension of N&-(endo-2-norbornyl)-9-MA (6 g, 24.66 mmoles) in 150 ml of IM sodium acetate buffer (pH 3.9) was added a solution of bromine (3.0 ml) in 300 ml of IM sodium acetate buffer (pH 3.9). The mixture was stirred overnight and the resulting precipitate was filtered and washed with water. To the residue was added silica gel and the suspension was evaporated to a powder. The powder was added to a silica gel column (150 g, packed with petroleum ether). The purine was eluted with 10% to 25% ethylacetate in petroleum ether. Evaporation of the appropriate fractions gave 6.7 g, 84% yield of $N^6$-(endo-2-norbornyl)-8-bromo-9-MA.

Preparation of $N^6$-(endo-2-norbornyl)-8-azido-9-MA

To a solution of $N^6$-(endo-2-norbornyl)-9-bromo-9-MA (0.72 g, 2.23 mmoles) in DMF was added sodium azide (0.91 g, 13.98 mmoles). The mixture was heated at 70°–80° C. overnight. The crude was dissolved in water, extracted with ethyl acetate, and then dried over magnesium sulfate and the organic phase was evaporated in vacuo to give 0.62 g, 98% yield.

Preparation of $N^6$-(endo-2-norbornyl)-8-amino-9-MA

The crude product, $N^6$-(endo-2-norbornyl)-8-Azido-9-MA (0.5 g, 1.75 mmole) was dissolved in ethanol. The solution, in presence of 10% palladium on charcoal (1 g), was shaken with H$_2$ at 35 atm overnight. The suspension was filtered and evaporated to a small volume, and then poured through a C-18 column (HPLC) to give 0.36 g 80% yield of $N^6$-(endo-2-norbornyl)-8-Amino-9-MA.

Preparation of $N^6$-(endo-2-norbornyl)-8-oxo-9-MA

To a mixture of $N^6$(endo-2-norbornyl)-9-Bromo-9-MA (0.15 g, 0.62 mmole) in 12 ml aoetic acid was added sodium acetate (0.5 g) and 1.2 ml acetic anhydride. The mixture was allowed to reflux overnight. The mixture was then evaporated under vacuo and purified on a chromatotron using CHCL$_1$, stepping to 2% ethanol, and finally to 4% ethanol on 2 mm plate giving 90 mg, 75% yield of $N^6$-(endo-2-norbornyl)-8-Oxo-9-MA.

Preparation of $N^6$-(endo-2-norbornyl)-8-cyclopentylamine-9-MA.

To a solution of $N^6$-(endo-2-norbornyl)-8-Bromo-9-MA (0.5 g, 1.55 mmoles) in 20 ml ethanol was added 20 ml of cyclopentylamine; the reaction mixture was refluxed overnight. The mixture was then evaporated under vacuo and passed through a C-18 column (HPLC) to give 0.32 g, 77% yield of $N^6$-(endo-2-norbornyl)-8-cyclopentylamine-9-MA.

Preparation of $N^6$-(endo-2-norbornyl)8-bromo-2-chloro-9-MA.

N4(endo-2-norbornyl)2-chloropurine was first prepared as follows: A mixture of 2,6-dichloropurine (5.0 g, 26.45 mmoles) endo-2-aminobornane hydrochloride (5.0 g, 33.86 mmoles) and triethyl amine (10 ml) in absolute ethanol was refluxed for 48 hours. The solution was then cooled to room temperature and evaporated in vacuo to a white solid. The white solid was washed with water and dried to yield 6.0 g. 84% yield of $N^6$-(endo-2-norbornyl)2-Chloropurine used as is with no further purification for next step.

A mixture of $N^6$-(endo-2-norbornyl)-2-chloropurine (5.0 g, 18.96 mmoles), triethyl ammonium hydroxide (18.9 ml), and methyl iodide (1.41 ml, 22.68 mmoles) in dichloromethane was heated to 35° C. for 24 hours. The solution was then evaporated in vacuo and the syrup was crystallized in methanol to give 4.0 g, 76% yield of $N^6$-(endo-2-norbornyl)2-chloro-9-MA.

To a stirred solution of $N^6$-(endo-2-norbornyl)-2-chloro-9-MA (4.3 g, 14.4 mmoles) in acetate buffer (1 molar acetic acid and 1 M sodium acetate mixture, 45:1 ratio respectively; pH 3.9) was added dropwise Bromine (3.12 g, 19.56 mmoles) dissolved in the acetate buffer. The reaction mixture was stirred for 72 hours; the mixture was then filtered and the solid material collected was eluted from ethyl acetate/petroleum ether on silica gel column to yield 4.9 g, 85% of $N^6$-(endo-2-norbornyl)8-Bromo-2-Chloro-9-MA. Preparation of $N^6$-(endo-2-norbornyl)-8-cyclopentyl-9-MA.

To a vigorously stirred solution of 2 g (12.2 mmoles) of 4-methylamino-5-amino-6-chloropyrimidine in CHCl$_3$ was added dropwise over a period of 20 minutes cyclopentane carbonyl chloride (1.6 g, 12.2 mmoles). The mixture was stirred overnight and then evaporated in vacuo to a yellow syrup. The syrup was then dissolved in methanol and purified through a C-18 column (HPLC) to give 2.2 g, 71% yield of 4 methylamino-6-chloro-5-cyclopentylamido-pyrimidine.

4-methylamino-6-chloro-5-cyclopentylamido-pyrimidine 2.2 g, 8.6 mmoles) was refluxed in POCl$_3$ for approximately 2 hours. The solution was concentrated in vacuo to a syrup. The syrup was added dropwise to ice. The aqueous mixture was then extracted with chloroform. The organic layer was evaporated and the syrup was passed through a C-18 column (HPLC) giving 1.25 g, 63% yield of 8-cyclopentyl-6-chloro-9-methyl adenine.

A mixture of 8-cyclopentyl-6-chloro-9-methyl adenine (0.48 g, 2.0 mmoles) and endo-2-aminonorbornane hydrochloride (0.5 g, 3.4 mmoles) in absolute ethanol was refluxed for 48 hours. The mixture was then evaporated in vacuo and purified through a C-18 column (HPLC) to give 0.45 g, 71% yield of $N^6$-(endo-2-norbornyl)-8-cyclopentyl-9-MA.

Preparation of $N^6$-(endo-2-norbornyl)-8-chloro-9-MA.

A mixture of $N^6$-(endo-2-norbornyl)-8-bromo-9-MA (1.25 g, 3.7 mmoles) and POCl$_3$ was refluxed for 1 hour. Then the phosphorous oxychloride was removed in vacuo and the yellow solid was passed through a C-18 column (HPLC) to give 0.96 g, 84% yield of $N^6$-(endo-2-norbornyl)-8-chloro-9-MA.

Preparation of $N^6$-(endo-2-norbornyl)-9-[(2-hydroxyethoxy) methyl]purine.

To a solution of 6-chloropurine (6 g, 38.8 mmoles) in DMF was added sodium hydride 60% (0.93 g) over 1.5 hour period. (2-acetoxyethoxy)methyl bromide was then added at room temperature; the reaction mixture was allowed to stir for 2 hours under Nz atmosphere. H$_2$O was added and the product was extracted with ethyl acetate. The organic phase was dried over MgSO4, filtered, and evaporated in vacuo to give a light yellow solid 7.1 g, 68% yield of 9-[(2-acetoxyethoxy)methyl]-6-chloro-purine. The crude was used without further purification.

To a solution of 9-[(2-acetoxyethoxy)methyl]-6-chloro-purine (5.1 g, 18.8 mmoles) in ethanol and triethylamine was added endo-2-aminonorbornane hydrochloride (4.0 g, 27.1 mmoles). The mixture was refluxed in vacuo and the residue was purified by HPLC to give 4.70 g, 77% yield of $N^6$-(endo-2-norbornyl)-9-[(2-acetoxyethoxy)methyl]purine.

A solution of $N^6$-(endo-2-norbornyl)-9-[(2-acetoxyethoxy) methyl]purine (3.75 g, 10.8 mmoles) in methanol was saturated with $NH_3$ gas under $N_2$. The mixture was stirred overnight, then evaporated in vacuo to give 2.03 g, 62% yield of $N^6$-(endo-2-norbornyl)-9-[(2-hydroxyethoxy)methyl]purine.

The invention is further illustrated by the following examples which are illustrative of various aspects of the invention. These examples are not intended as limiting the scope of the invention as defined by the appended claims.

PHARMACOLOGIC TESTING

A series of $N^6$-substituted 9-methyladenines were L assayed as adenosine antagonists in $A_1$ and $A_2$ test systems (Ukena, et.al., FEBS Lett. 215(2), 203-208, 1987). For activity at $A_1$ receptors, compounds were tested as inhibitors of the binding of $N^6$-R-[$^3$H]-Phenylisopropyladenosine in rat brain membranes and for their ability to prevent R-PIA-induced inhibition of adenylate cyclase in rat fat cell membranes. For activity at $A_2$ receptors, compounds were tested as antagonists of NECA-stimulated adenylate cyclase in membranes of human platelets and rat PC12 cells.

It is known that $A_1$ receptors influence inhibition of adenylate cyclase in fat, brain and heart cells; whereas $A_2$ receptors stimulate adenylate cyclase in endothelial and smooth muscle cells. (See John W. Daly, et.al., "Structure -Activity Relationship for $N^6$-Substituted Adenosines at a Brain $A_1$-Adenosine Receptor With A Comparison to an $A_2$-Adenosine Receptor Regulating Coronary Blood Flow," Biochemical Pharmacology, Vol. 35. No. 15, pp. 2467-2471 (1986)).

The results summarized below in Table 1 show that $N^6$ substitution can markedly increase the potency of 9-methyladenine at adenosine receptors. The lower apparent affinity values ($K_B$, $K_i$) identify the most potent compounds. The most pronounced effect is seen at $A_1$ receptors. For example, $N^6$-cyclopentyl-9-methyladenine is at least 100-fold more potent than 9-methyladenine at $A_1$ receptors. At $A_2$ receptors, this compound is fivefold more potent than 9-methyladenine in the human platelet assay. Thus, this data demonstrates the activity of a novel series of adenosine antagonists.

TABLE 1

| | $A_2$ Effects | | $A_1$ Effects | |
|---|---|---|---|---|
| | $K_B$ (µM) vs NECA Stimulation (Adenylate Cyclase) | | $K_B$ (µM) vs PIA INHIBITION (Adenylate Cyclase) | $K_i$ (µM) vs [$^3$H] PIA (Binding) |
| | (A) | (B) | (C) | (D) |
| 1. Adenine | 760 | 570 | >1000 | >100 |
| 2. 9-Methyladenine (9-MA) | 24 | 24 | 112 | 106 |
| $N^6$-substituted 9-methyladenines | | | | |
| 3. $N^6$-Cyclobutyl-0-MA | 5.5 | 23 | 0.89 | 1.2 |
| 4. $N^6$-Cyclopentyl-9-MA | 4.9 | 25 | 1.3 | 0.54 |
| 5. $N^6$-Methylcylopentyl-9-MA | 45 | 56 | 9.0 | 2.5 |
| 6. $N^6$-Cyclohexyl-9-MA | 7.4 | 21 | 0.65 | 0.94 |
| 7. $N^6$-Methyl-9-MA | 150 | 130 | 220 | >100 |
| 8. $N^6$-3-Pentyl-9-MA | 11 | 53 | 7.6 | 3.3 |
| 9. $N^6$-Phenyl-9-MA | 21 | 107 | 10 | 25 |
| 10. $N^6$-2-Fluorophenyl-9-MA | 11 | 29 | 17 | 8.5 |
| 11. $N^6$-2-Benzyl-9-MA | 57 | 100 | 49 | 17 |
| 12. $N^6$-2-Phenethyl-9-MA | 170 | 120 | >300 | >100 |
| 13. $N^6$-2-(3,4,5-Trimethoxyphenylethyl)-9-MA | 23 | 40 | 122 | >100 |
| 14. $N^6$-2-(3-Pyridylethyl)-9-MA | 92 | 117 | 96 | 41 |
| 15. $N^6$-2-(3-Thienylethyl)-9-MA | 14 | 25 | 24 | 20 |
| 16. $N^6$-R-1-Phenyl-2-propyl-9-MA | 13 | 25 | 7.2 | 2.5 |
| 17. $N^6$-S-1-Phenyl-2-propyl-9-MA | 23 | 74 | 23 | 10 |

(A) - Human Platelet Membranes
(B) - Rat PC12 Membranes
(C) - Rat Fat Cell Membranes
(D) - Rat Brain Membranes

FURTHER FUNCTIONAL ASSAYS

To test the selectivity of the compounds of the invention, in vitro assays were conducted utilizing model tissues that are thought to contain homogeneous populations of either the $A_1$ or $A_2$ adenosine receptors. Four examples were characterized by their ability to antagonize competitively the action of adenosine agonists in eliciting two responses: the reduction in force of contraction of guinea pig atrium ($A_1$); and the decrease in the contractile tone of the guinea pig taenia caecum ($A_2$).

The left atria from male guinea pigs were isolated, suspended between two punctate electrodes, and placed in a 20 ml organ bath that contained Krebs-Hensileit solution that was continuously gassed with 95% $O_2$+5% $CO_2$ and maintained at 31° C. The resting tension was one gram. The atria were stimulated electrically at 1 Hz, 1 msec duration pulses at supramaximal voltage. The force of contraction was recorded isometrically.

Taenia from the guinea pig caecum were cut into lengths of 1.5-2 cm. The tissues were suspended in a 20 ml organ bath containing de Jalon's solution that was gassed with 95% $O_2$+5% $CO_2$ and maintained at 31° C. The resting tension was 1.5 g. The contractile response was measured isotonically. Tissues were contracted with $10^{-7}$M 5-methylfurmethide and allowed sufficient time to reach a stable contraction before addition of adenosine agonists.

The ability of the compounds to antagonize the effects of agonists was analyzed using modified Schild plots.

Although there was some sensitization of the tissue, i.e. addition of the agonist produced a larger response in the presence of high concentrations of the subject compounds, $N^6$-3-Pentyl-9-MA, $N^6$-cyclopentyl-9-MA and $N^6$-(endo-2-norbornyl)-9-MA did not competitively antagonize the effects of adenosine agonists in relaxing the taenia caecum. Sensitization is also observed when using high concentrations of 8-phenyltheophylline (8-PT), a non-selective adenosine receptor antagonist. 8-PT did antagonize the effects of agonists at low concentrations. The lack of competitive antagonism by the other compounds suggests that the latter compounds do not interact appreciably with $A_2$-adenosine receptors and are, thus, selective for $A_1$ adenosine receptors.

However, $N^6$-3-Pentyl-9-MA, $N^6$-cyclopentyl-9-MA, $N^6$-(endo-2-norbornyl)-9-MA and $N^6$-4-(2-thienyl)-3-o butyl)-9-MA all were found to be competitive antagonists at adenosine receptors in the atria. $N^6$-3-Pentyl-9-MA and $N^6$-1-(2-thienyl)-2-butyl-9-MA also produced increases in basal force of contraction in the atria. Affinity constants ($pK_8$) for the present compounds determined using known methods are summarized in Table 2 below:

TABLE 2

| Drug | $pK_B$ |
|---|---|
| $N^6$-3-pentyl-9-MA | 5.4 ± 0.14 |
| $N^6$-cyclopentyl-9-MA | 6.17 ± 0.11 |
| $N^6$-(endo-2-norbornyl)-9-MA | 6.28 ± 0.09 |
| $N^6$-1-(2-thienyl)-2-butyl)-9-MA | 5.36 ± 0.1 |

These results show that the above examples display selectivity towards the $A_1$ adenosine receptor, with $N^6$-(endo-2-norbornyl)-9-MA being the most potent antagonist.

L. IN VIVO ASSAY

In vitro selectivity of the present antagonists was confirmed by in vivo tests on rat heart rate and blood pressure, the former associated with $A_1$ receptors and the latter associated with $A_2$ receptors.

Rats were anesthetized with urethan and blood pressure was monitored via a carotid cannula. Drug injections were made intravenously through a jugular cannula. Blood pressure, EGC, and heart rate were recorded on a Grass polygraph.

Adenosine produced a dose dependent decrease in blood pressure and heart rate, with a concomitant increase in the P-R interval of the ECG. Administration of $N^6$-(endo norbornyl)-9-methyladenine attenuated the effects of subsequently administered adenosine on all parameters measured. At high doses, adenosine causes heart block; this effect was also substantially reduced by the agonist. Due to the short duration of action and direct route of administration of adenosine, it is often difficult to determine whether adenosine decreased blood pressure by causing peripheral vasodilation or by reducing cardiac output To overcome tese problems, NECA (5'-N-ethylcarboxamide adenosine), which is longer-acting and selective for $A_2$ adenosine receptors, was used as an adenosine receptor agonist. Prior administration of N-0861 attenuated the effects of NECA on the heart while minimally affecting the NECA-induced decrease in blood pressure. These results show that $N^6$-endo-2-norbornyl)-9-methyladenine is a cardioselective adenosine receptor antagonist in vivo and support the data above showing selectively of the $N^6$ substituted 9-methyladenines of the invention as $A_1$ adenosine receptor antagonists.

FURTHER RECEPTOR AFFINITY ASSAYS

Further tests to discover the affinities of test compounds at $A_2$ receptors were conducted. [$^3$H]-N-ethylcarboxamido adenosine ([$^3$H-]-NECA) was used as the radioligand, bovine caudate was the source of membranes, and the assay buffer was 50 mM Tris; 10 mM $MgCl_2$, pH 7.4.

To provide bovine caudate nuclei, bovine brains were obtained fresh from a local slaughterhouse. The caudate nuclei were dissected out and homogenized in Buffer A (50 mm Tris; 1 mm $Na_2$-EDTA; 5 mm KCl; 1 mm $MgCl_2$; 2 mm $CaCl_2$; pH 7.4) using a Brinkman Polytron. The homogenate was centrifuged at 40,000×g for 20 minutes and washed once. The pellet was resuspended in Buffer A, incubated at 37° C. for 15 minutes, then centrifuged. The pellet was washed once more, resuspended to a protein concentration of 5–10 mg/ml in Buffer A and frozen at −70° C. until use.

The $A_2$ assays also contained 50 cyclopentyl-adenosine to block the binding of [$^3$H]-NECA to $A_1$ receptors (Bruns et.al., 1986) and 1 unit/ml adenosine deaminase to degrade endogenous adenosines. Varying concentrations of test compounds were incubated with the appropriate radioligand and membrane source for 1 hr at room temperature.

Assays were terminated by filtration over Whatman GF/B filters that had been pre-soaked with 0.1% polyethyleneimine using a 24 port Brandell cell hawester. The filters were washed three times with 3 ml of ice cold buffer and transferred to plastic scintillation vials to which 4 ml of Beckman Ready-Protein scintillation cocktail was added. The tubes were shaken and counted in a Beckman 3801 scintillation counter that converted cpm to dpm.

Data were analyzed by utilizing the Ligand commercial computer program (Munson and Rodbard, 1980).

The results of these tests, expressed as the molar concentration of test compound needed to displace 50 percent of the [$^3$H]-CHA radioligand from rat cortical $A_1$ receptors, are summarized in Table 3 below:

TABLE 3

| | Adenosine Antagonists | |
|---|---|---|
| Sample No. | Name | Rat Cortical Binding Constant $K_i$ (M) |
| 0861 | $N^6$-(endo-2-norbornyl)-9-MA | $11.6 \times 10^{-8}$ |
| 0913 | $N^6$-(endo-2-norbornyl)-2-chloro-9-MA | $10.5 \times 10^{-8}$ |
| 0966 | $N^6$-2,2-diphenylethyl-9-MA | $>10^{-5}$ |
| 0967 | $N^6$-2(2-chlorophenylethyl)9-MA | $>10^{-5}$ |
| 0982 | $N^6$-2-Aminoethyl-9-MA | $>10^{-5}$ |
| 0983 | $N^6$-(2,2-N-dimethylethyl)-9-MA | $>10^{-5}$ |
| 0840 | $N^6$-cyclopentyl-9-MA | $37.5 \times 10^{-8}$ |
| 0984 | $N^6$-R-1-phenyl-1-ethyl-9-MA | $>10^{-5}$ |
| 0985 | $N^6$-S-1-phenyl-1-ethyl-9-MA | $>10^{-4}$ |
| 0986 | $N^6$-S-1-phenyl-2-propyl-9-MA | $>10^{-5}$ |
| 0987 | N6 2-thienyl-9-MA | $>10^{-4}$ |
| 0988 | N6(4-chloro-2-methylphenyl)-9-MA | $>10^{-5}$ |
| 0989 | $N^6$-2-(3-ethylindole)-9-MA | $>10^{-5}$ |
| 0990 | $N^6$-2-(phenethyl)9-MA | $>10^{-5}$ |
| 1001 | $N^6$-(endo-2-norbornyl)-8-oxo-9-MA | $\approx 10^{-5}$ |
| 1002 | $N^6$-2-(3,4,5-trimethoxyphenyl)ethyl-9-MA | $>10^{-5}$ |
| 1003 | $N^6$-(endo-2-norbornyl)-8-bromo-9-MA | $1.3 \times 10^{-8}$ |
| 1004 | $N^6$-1-carboxy-1-butyl-9-MA | $>10^{-4}$ |
| 1005 | $N^6$-(endo-2-norbornyl)-8-amino-9-MA | $87 \times 10^{-8}$ |

TABLE 3-continued

Adenosine Antagonists

| Sample No. | Name | Rat Cortical Binding Constant $K_i$ (M) |
|---|---|---|
| 1006 | $N^6$-(endo-2-norbornyl)-8-carboxy-9-MA Sodium Salt | $> 10^{-5}$ |
| 1059 | $N^6$-(endo-2-norbornyl)9-[(2 hydroxyethoxy)methyl]adenine | $49 \times 10^{-8}$ |
| 1060 | $N^6$-(endo-2-norbornyl)-8-thio-9-MA | $37 \times 10^{-8}$ |
| 1061 | $N^6$-(endo-2-norbornyl)-8-chloro-9-MA | $1.5 \times 10^{-8}$ |
| 1062 | $N^6$-(endo-2-norbornyl)-8-sulfonate-9-MA Sodium Salt | $> 10^{-4}$ |
| 1063 | $N^6$-(Endo-2-norbornyl)-2-oxo-9-MA | $112 \times 10^{-8}$ |
| 1064 | $N^6$-(endo-2-norbornyl)-8-cyclopentylamine-9-MA | $190 \times 10^{-8}$ |
| 0964 | $N^6$-(endo-2-norbornyl)-8-cyclopentyl-9-MA | $24 \times 10^{-8}$ |
| 0965 | $N^6$-cyclopentyl-8-cyclopentyl-9-MA | $14.1 \times 10^{-8}$ |
| 0978 | $N^6$-(exo-2-norbornyl)-9-MA | $43 \times 10^{-8}$ |

The compounds in Table 3 for which a solution having a concentration greater than $10^{-5}$M was required to displace 50 percent of the radioligand are deemed ineffective as $A_1$ adenosine receptor antagonists.

In further experiments designed to determine the selectivity of $N^6$-endo-2-norbornyl-9-methyl adenine at $A_1$ receptors, [$^3$H]-cyclohexyladenosine ([$^3$H]-CHA) was used as the radioligand, rat cortical membranes were the receptor source, and the assay buffer was 50 mM Tris; 2 mM $MgCl_2$ pH 7.4.

Male Sprague Dawley rats were killed by decapitation and the brains removed. The cerebral cortices were homogenized in 50 mm Tris; 2mm $MgCl_2$ (pH 7.4), and centrifuged at $40,000 \times g$ for 10 minutes. The pellet was washed once, resuspended in Tris/$MgCl_2$ and incubated with 8 units/ml adenosine deaminase at 37° C. for 30 minutes. The homogenate was centrifuged, washed once, resuspended to a protein concentration of 5–10 mg/ml and frozen at $-70°$ C. until use. The results in Table 4 below show that the test compound has 170 times more affinity for $A_1$ receptors than for $A_2$ receptors.

TABLE 4

Selectivity of $N^6$-endo-2-Norbornyl-9-MA Bovine Caudate Binding Constants

| At $A_1$ Receptors $K_i$ (M) | At $A_2$ Receptors $K_i$ (M) |
|---|---|
| $4.1 \times 10^{-8}$ M | $6.96 \times 10^{-6}$ M $A_1/A_2 = 5.89 \times 10^{-3}$ = 170 fold selective for $A_1$ receptors |

References Munson, Peter J. and Rodbard, David (1980). "Ligand: A Versatile Computerized Approach for Characterizing Ligand-Binding Systems." *Anal. Biochem.* 107:220–239. Bruns, Robert F., Lee, Gina H., and Pugsley, Thomas A. (1986) "Characterization of the $A_2$ Adenosine Receptor Labeled by $^3$H-NeCA in Rat Striatal Membranes," *Mol. Pharmaool.* 29:331–346.

These $N^6$-substituted adenines are antagonists of $A_2$-adenosine receptor-mediated stimulation of adenylate cyclase in $A_2$-adenosine receptors and antagonists of $A_1$-adenosine receptor-mediated inhibition of adenylate cyclase. These compounds are useful in reversal of adenosine-mediated lipolysis, reversal of adenosine-mediated deleterious cardiovascular effects (conduction defects, hypotension), reversal of adenosine-mediated vascular actions in kidney, bronchodilation, antiarrhythmic action, reversal of adeno-mediated relaxation of smooth muscle, anti-narcoleptic action, CNS stimulation, and blockade of adenosine mediated inhibition of neurotransmitter release.

It should be appreciated that while the present method for determining the viability of tissue has been disclosed in combination with imaging utilizing a blood marking medium, the present invention is also useful in combination with any other method for examination of tissue such as ultrasonic or NMR (Nuclear Magnetic Resonance).

What is claimed is:

1. A method for determining the viability of tissue in a region of an organism having a vascular circulatory system that supplies blood to said region which comprises the steps of:

(a) dilating said vascular circulation system by introducing adenosine or an adenosine agonist into said vascular circulation system in order to increase the flow of blood into said region;

(b) introducing a blood flow marking medium into said region;

(c) alleviating the non-dilating effects of adenosine or said adenosine agonist by introducing an $A_1$ adenosine receptor antagonist into said vascular circulatory system; and (d) determining the amount of marking medium in said region.

2. The method of claim 1 wherein the $A_1$ adenosine receptor agonist is

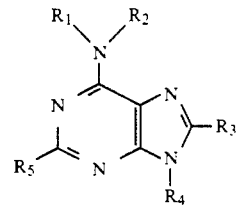

wherein $R_1$ is hydrogen or $R_2$; $R_2$ is selected from the group consisting of endo-2-norbornyl or cyclopentyl; $R_3$ is selected from the group consisting of hydrogen, halogen, amine, carboxy, alkyl radicals having 1 to 10 carbon atoms, cycloalkyl radicals having from 3 to 8, preferably 5 to 6, ring carbon atoms, thio, sulfonate, sulfonamide, sulfon, sulfoxamide, phenyl, alkyl-substituted amine, and cycloalkyl substituted amine; is selected from the group consisting of benzyl, phenyl, and alkyl groups comprising from 1 to 4 carbon atoms, wherein said alkyl group can be substituted with oxygen, for instance ethers and alcohols; and $R_5$ is selected from the group consisting of hydrogen; hydroxy; sulfonate; halogen; alkoxy and cycloalkoxy groups comprising 1 to 6 carbon atoms.

3. The method of claim 1 wherein the $A_1$ adenosine receptor agonist is an $N^6$-norbornyl substituted adenine.

4. The method of claim 3 wherein the $A_1$ adenosine receptor agonist is selected from the group consisting of:

$N^6$-(endo-2-norbornyl)-9-methyl adenine,
$N^6$-(endo-2-norbornyl)-2-chloro-9-methyl adenine,
$N^6$-(endo-2-norbornyl)-8-bromo-9-methyl adenine,
$N^6$-(endo-2-norbornyl)-8-amino-9-methyl adenine,
$N^6$-(endo-2-norbornyl)-9-[(2-hydroxyethoxy)methyl]adenine,
$N^6$-(endo-2-norbornyl)-8-thio-9-methyl adenine,
$N^6$-(endo-2-norbornyl)-8-chloro-9-methyl adenine, N6-(endo-2-norbornyl)-2-oxo-9-methyl adenine,
N6-(endo-2-norbornyl)-8-cyclopentyl-amine-9-methyl adenine,
N6-(endo-2-norbornyl)-8-cyclopentyl-9-methyl adenine, and
N6-(exo-2-norbornyl)-9-methyl adenine.

5. The method of claim wherein the $A_1$ adenosine receptor agonist is selected from the group consisting of N6-3-pentyl-9-methyl adenine, N6-cyclopentyl-9-methyl adenine, N6-1-(2-thienyl)-2-butyl-9-methyl adenine, and N6-cyclopentyl-8-cyclopentyl-9-ethyl adenine.

6. The method of claim 1 wherein said marking medium is selected from the group consisting of thallium-201 and rubidium-82.

7. The method of claim 6 wherein said marking medium comprises thallium-201.

8. The method of claim 7 wherein adenosine is introduced into said vascular circulatory system.

9. The method of claim 8 wherein the amount of marking medium in said region is determined by noninvasive myocardial imaging of the blood flow to said region.

10. The method of claim 3 wherein said N6-norbornyl substituted adenine is N6-(endo-norbornyl)-9-methyl adenine.

11. A method for determining the viability of tissue in a region of an organism having a vascular circulatory system that supplies blood to said region which comprises the steps of:
    (a) dilating said vascular circulation system by introducing adenosine or an adenosine agonist into said vascular circulation system in order to increase the flow of blood into said region;
    (b) introducing a blood flow marking medium into said region;
    (c) reducing the amount of adenosine or said adenosine agonist necessary to dilate the vascular circulation system by introducing an A adenosine receptor antagonist into said vascular circulatory system; and
    (d) determining the amount of marking medium in said region.

12. The method of claim 11 wherein the $A_1$ adenosine receptor agonist is

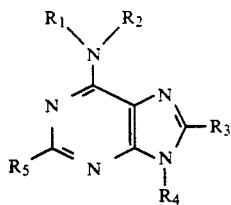

wherein $R_1$ is hydrogen or $R_2$; $R_2$ is selected from the group consisting of endo-2-norbornyl or cyclopentyl; $R_3$ is selected from the group consisting of hydrogen, halogen, amine, carboxy, alkyl radicals having 1 to 10 carbon atoms, cycloalkyl radicals having from 3 to 8, preferably 5 to 6, ring carbon atoms, thio, sulfonate, sulfonamide, sulfon, sulfoxamide, phenyl, alkyl-substituted amine, and cycloalkyl substituted amine; $R_4$ is selected from the group consisting of benzyl, phenyl, and alkyl groups comprising from 1 to 4 carbon atoms, wherein said alkyl group can be substituted with oxygen, for instance ethers and alcohols; and $R_5$ is selected from the group consisting of hydrogen; hydroxy; sulfonate; halogen; alkoxy and cycloalkoxy groups comprising 1 to 6 carbon atoms.

13. The method of claim 11 wherein the $A_1$ adenosine receptor agonist is an N6-norbornyl substituted adenine.

14. The method of claim 31 wherein the $A_1$ adenosine receptor agonist is selected from the group consisting of:
N6-(endo-2-norbornyl)-9-methyl adenine,
N6-(endo-2-norbornyl)-2-chloro-9-methyl adenine,
N6-(endo-2-norbornyl)-8-bromo-9-methyl adenine,
N6-(endo-2-norbornyl)-8-amino-9-methyl adenine,
N6-(endo-2-norbornyl)-9-[(2-hydroxyethoxy)methyl]adenine,
N6-(endo-2-norbornyl)-8-thio-9-methyl adenine,
N6-(endo-2-norbornyl)-8-chloro-9-methyl adenine,
N6-(endo-2-norbornyl)-2-oxo-9-methyl adenine,
N6-(endo-2-norbornyl)-8-cyclopentyl-amine-9-methyl adenine,
N6-(endo-2-norbornyl)-8-cyclopentyl-9-methyl adenine, and
N6-(exo-2-norbornyl)-9-methyl adenine.

15. The method of claim 11 wherein the $A_1$ adenosine receptor agonist is selected from the group consisting of N6-3-pentyl-9-methyl adenine, N6-cyclopentyl-9-methyl adenine, N6-1-(2-thienyl)-2-butyl-methyl adenine, and N6-cyclopentyl-8-cyclopentyl-9-methyl adenine.

16. The method of claim 11 wherein said marking medium is selected from the group consisting of thallium-201 and rubidium-82.

17. The method of claim 16 wherein said marking medium comprises thallium-201.

18. The method of claim 17 wherein adenosine is introduced into said vascular circulatory system.

19. The method of claim 18 wherein the amount of marking medium in said region is determined by noninvasive myocardial imaging of the blood flow to said region.

20. The method of claim 19 wherein said N6-norbornyl substituted adenine is N6-(endo-norbornyl)-9-methyl adenine.

21. In a method for determining the viability of tissue in a region of an organism having a vascular circulatory system that supplies blood to said region the improvement which comprises the steps of;
    (a) dilating said vascular circulation system by introducing adenosine or an adenosine agonist into said vascular circulation system in order to increase the flow of blood into said region; and,
    (b) alleviating the non-dilating effects of adenosine or said adenosine agonist by introducing an Al adenosine receptor antagonist into said vascular circulatory system.

* * * * *

UNITED STATES PATENT AND TRADEMARK OFFICE
CERTIFICATE OF CORRECTION

PATENT NO. : 5,117,830

DATED : June 2, 1992

INVENTOR(S) : Donald A. McAfee et al.

It is certified that error appears in the above-identified patent and that said Letters Patent is hereby corrected as shown below:

Title page, item [57]:
Abstract, line 14, reads "adenosine agonist" and should read --adenosine antagonist--.

Column 12:
Claim 2, line 2, reads "receptor agonist" and should read --receptor antagonist--.

Claim 2, line 8, the phrase "preferably 5 to 6," should be deleted.

Claim 2, line 13, reads "can be" and should read --is--.

Claim 2, line 14, the phrase "for instance ethers and alcohols" should be deleted.

Claim 3, line 2, reads "receptor agonist" and should read --receptor antagonist--.

Claim 4, line 2, reads "receptor agonist" and should read --receptor antagonist--.

Column 13:
Claim 5, line 2, reads "receptor agonist" and should read --receptor antagonist--.

Claim 11, line 13, reads "A adenosine" and should read --$A_1$ adenosine--.

Claim 12, line 2, reads "receptor agonist" and should read --receptor antagonist--.

Claim 12, line 8, the phrase "preferably 5 to 6," should be deleted.

UNITED STATES PATENT AND TRADEMARK OFFICE
CERTIFICATE OF CORRECTION

PATENT NO. : 5,117,830

Page 2 of 2

DATED : June 2, 1992

INVENTOR(S) : Donald A. McAfee et al.

It is certified that error appears in the above-identified patent and that said Letters Patent is hereby corrected as shown below:

Claim 12, line 13, reads "can be" and should read --is--.
Column 14:
Claim 12, line 14, the phrase "for instance ethers and alcohols" should be deleted.

Claim 13, line 2, reads "receptor agonist" and should read --receptor antagonist--.

Claim 14, line 2, reads "receptor agonist" and should read --receptor antagonist--.

Claim 15, line 2, reads "receptor agonist" and should read --receptor antagonist--.

Signed and Sealed this

Twentieth Day of September, 1994

Attest:

BRUCE LEHMAN

Attesting Officer

Commissioner of Patents and Trademarks